(12) United States Patent
Kim et al.

(10) Patent No.: US 9,880,381 B2
(45) Date of Patent: Jan. 30, 2018

(54) VARIFOCAL LENS, OPTICAL SCANNING PROBE INCLUDING THE VARIFOCAL LENS, AND MEDICAL APPARATUS INCLUDING THE OPTICAL SCANNING PROBE

(71) Applicant: SAMSUNG ELECTRONICS CO., LTD., Suwon-si (KR)

(72) Inventors: Woon-bae Kim, Seoul (KR); Seung-wan Lee, Suwon-si (KR); Eun-sung Lee, Hwaseong-si (KR); Min-seog Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 739 days.

(21) Appl. No.: 14/446,849

(22) Filed: Jul. 30, 2014

(65) Prior Publication Data

US 2015/0094599 A1 Apr. 2, 2015

(30) Foreign Application Priority Data

Sep. 27, 2013 (KR) .......................... 10-2013-0115706

(51) Int. Cl.
*G02B 26/10* (2006.01)
*G02B 3/14* (2006.01)
(Continued)

(52) U.S. Cl.
CPC .............. *G02B 26/103* (2013.01); *G02B 3/14* (2013.01); *G02B 15/00* (2013.01); *A61B 5/0066* (2013.01); *A61B 5/0095* (2013.01)

(58) Field of Classification Search
CPC .. A61B 5/0066; A61B 5/0095; G02B 26/103; G02B 15/00
See application file for complete search history.

(56) References Cited

U.S. PATENT DOCUMENTS 6,134,003 A 10/2000 Tearney et al.
6,608,684 B1 8/2003 Gelikonov et al.
(Continued)

FOREIGN PATENT DOCUMENTS

KR 10-2013-0030104 A 3/2013
KR 10-2013-0081467 A 7/2013

OTHER PUBLICATIONS

Weber, Niklas et al., "A Tunable Optofluidic Silicon Optical Bench," Journal of Microelectromechanical Systems, vol. 21, No. 6, Dec. 2012, pp. 1357-1364.

*Primary Examiner* — Joseph Dietrich
(74) *Attorney, Agent, or Firm* — Sughrue Mion, PLLC

(57) ABSTRACT

A varifocal-type optical scanning probe including an optical fiber scanner and a varifocal lens is provided. The varifocal lens includes: a first membrane lens comprising a first lens surface with a variable curvature and a first pressure surface configured to induce a curvature variation of the first lens surface; a second membrane lens including a second lens surface with a variable curvature and a second pressure surface configured to induce a curvature variation of the second lens surface; a first pressure member disposed to apply a pressure to the first pressure surface; a second pressure member disposed to apply a pressure to the second pressure surface; and a motor configured to transmit a driving force to at least one of the first pressure member and the second pressure member.

21 Claims, 10 Drawing Sheets

(51) Int. Cl.
    *G02B 15/00*    (2006.01)
    *A61B 5/00*    (2006.01)

(56) References Cited

U.S. PATENT DOCUMENTS

| | | |
|---|---|---|
| 7,283,247 B2 | 10/2007 | Okawa et al. |
| 7,602,557 B2 | 10/2009 | Berge et al. |
| 7,616,986 B2 | 11/2009 | Seibel et al. |
| 8,411,366 B2 | 4/2013 | Choi et al. |
| 2009/0180198 A1* | 7/2009 | Lee .......................... G02B 3/14 359/666 |
| 2010/0002785 A1 | 1/2010 | Mantravadi et al. |
| 2011/0098572 A1 | 4/2011 | Chen et al. |
| 2012/0188510 A1 | 7/2012 | Suehira et al. |
| 2013/0070249 A1 | 3/2013 | Choi et al. |
| 2013/0177227 A1 | 7/2013 | Lim et al. |
| 2014/0005532 A1 | 1/2014 | Choi et al. |
| 2014/0146324 A1 | 5/2014 | Lim et al. |

* cited by examiner

VARIFOCAL LENS, OPTICAL SCANNING PROBE INCLUDING THE VARIFOCAL LENS, AND MEDICAL APPARATUS INCLUDING THE OPTICAL SCANNING PROBE

CROSS-REFERENCE TO RELATED APPLICATIONS

This application claims priority from Korean Patent Application No. 10-2013-0115706, filed on Sep. 27, 2013, in the Korean Intellectual Property Office, the disclosure of which is incorporated herein in its entirety by reference.

BACKGROUND

1. Field

Methods and apparatuses of the exemplary embodiments relate to varifocal lenses, optical scanning probes including the varifocal lenses, and medical apparatuses including the optical scanning probes.

2. Description of the Related Art

In the field of medical imaging, technology for accurately capturing information about a skin tissue and a tomogram thereunder is required. In particular, since most cancers occur under epithelial cells and spread into dermal cells in which blood vessels exist, damage caused by the cancers may be reduced when the cancers are detected in the early stages. Related art imaging technology, such as magnetic resonance imaging (MRI), computed tomography (CT), or ultrasound, may capture an inner tomogram through the skin, but may not detect an early stage of cancer if only a small number of cancerous cells exist. On the other hand, optical coherence tomography (OCT) technology may detect an early stage of cancer if the cancerous cells have a size of about 50 μm to about 100 μm since the OCT technology has a resolution which is about 10 times higher than the resolution of the ultrasound technology, and provides about 2 mm to about 3 mm smaller skin penetration depth than the related art imaging technology. However, the OCT technology does not currently provide sufficient resolution to replace biopsy and histology processes, which are actually used to detect cancers.

SUMMARY

Provided are varifocal lenses, optical scanning probes including the varifocal lenses, and medical apparatuses including the optical scanning probes.

Additional aspects will be set forth in part in the description which follows and, in part, will be apparent from the description, or may be learned by practice of the presented exemplary embodiments.

According to an aspect of the exemplary embodiment, a varifocal lens includes: a first membrane lens including a first lens surface with a variable curvature and a first pressure surface configured to induce a curvature variation of the first lens surface; a second membrane lens including a second lens surface with a variable curvature and a second pressure surface configured to induce a curvature variation of the second lens surface; a first pressure member configured to apply a pressure to the first pressure surface; a second pressure member configured to apply a pressure to the second pressure surface; and a motor configured to transmit a driving force to at least one of the first pressure member and the second pressure member.

According to the exemplary embodiment, the motor may be a linear motor configured to generate a linear driving force.

According to an aspect of the exemplary embodiment, the varifocal lens may further include a slider configured to move linearly according to the linear driving force of the motor, wherein the first pressure member and the second pressure member may be mounted on the slider such that the first pressure member and the second pressure member are spaced apart from each other by a predetermined distance in a linear movement direction of the motor.

According to an aspect of the exemplary embodiment, a first fixing member and a second fixing member, which are configured to respectively secure the first pressure member and the second pressure member onto the slider, may be attached to the slider.

According to an aspect of the exemplary embodiment, an elastic member may be further provided at one end of the slider, and the elastic member may be contracted when the linear driving force is transmitted from the motor and the slider moves forward, and may be restored to an original state to move the slider backward when the linear driving force is not transmitted from the motor.

According to an aspect of the exemplary embodiment, a support member may be further configured between the elastic member and the first pressure member to support the contraction of the elastic member.

According to another aspect of the exemplary embodiment, the varifocal lens may further include a lens base on which the support member, the first membrane lens, and the second membrane lens are assembled, wherein the lens base may have a groove portion that is recessed such that the slider moves linearly by being inserted into the groove portion.

According to another aspect of the exemplary embodiment, the first membrane lens and the second membrane lens may be configured such that the first lens surface and the second lens surface face in opposite directions. In this case, the first pressure member and the second pressure member may be configured on the slider such that the first pressure member pressurizes the first pressure surface and the second pressure member recedes from the second pressure surface when the motor is driven forward.

According to another aspect of the exemplary embodiment, the first membrane lens and the second membrane lens may be configured such that the first lens surface and the second lens surface face in the same direction. In this case, the first pressure member and the second pressure member may be configured on the slider such that the first pressure member applies a pressure to the first pressure surface and the second pressure member applies a pressure to the second pressure surface when the motor is driven forward.

According to another aspect of the exemplary embodiment, the first membrane lens and the second membrane lens may be configured such that the first lens surface and the second lens surface face each other. In this case, the first pressure member and the second pressure member may be configured on the slider such that the second pressure member applies a pressure to the second pressure surface and the first pressure member recedes from the first pressure surface when the motor is driven forward.

According to another aspect of the exemplary embodiment, the first membrane lens may further include a third pressure surface, and the second membrane lens may further include a fourth pressure surface. In this case, the varifocal lens may further include: a third pressure member configured to apply a pressure to the third pressure surface; and a fourth pressure member configured to apply a pressure to the fourth pressure surface.

According to another aspect of the exemplary embodiment, the first pressure member and the third pressure member may be configured in a direction perpendicular to a linear movement direction of the motor, and the second pressure member and the fourth pressure member may be configured in the direction perpendicular to the linear movement direction of the motor.

According to another aspect of the exemplary embodiment, the varifocal lens may further include: a third fixing member connected to the first fixing member; and a fourth fixing member connected to the second fixing member, wherein the third pressure member and the fourth pressure member may be mounted on the slider by the third fixing member and the fourth fixing member, respectively.

According to an exemplary embodiment, the third pressure member and the fourth pressure member may not be mounted on the slider, and may be configured to respectively pressurize the third pressure surface and the fourth pressure surface by a predetermined pressure to form an initial curvature of the first lens surface and an initial curvature of the second lens surface.

According to another aspect of the exemplary embodiment, the third pressure member and the fourth pressure member may be screw-shaped, and a third fixing member and a fourth fixing member, which are a screw-fastening type, may be provided corresponding to the third pressure member and the fourth pressure member, to adjust a pressurized level of the third pressure surface and a pressurized level of the fourth pressure surface, respectively.

According to another aspect of the exemplary embodiment, the motor may include: a first motor configured to transmit a linear driving force to the first pressure member; and a second motor configured to transmit a linear driving force to the second pressure member.

According to another aspect of the exemplary embodiment, the first membrane lens and the second membrane lens may be spaced apart from each other in a direction of the linear driving force and may be spaced apart from each other in a direction perpendicular to the direction of the linear driving force.

According to another aspect of the exemplary embodiment, an optical scanning probe includes: an optical fiber scanner; and any one of the above-described varifocal lenses configured to focus light from the optical fiber scanner onto an object.

According to the exemplary embodiment, the optical scanning probe may further include a controller configured to control the motor such that a focal length of the varifocal lens corresponds to a focal length implementing a numerical aperture (NA) and a depth of focus (DOF) suitable for an optical coherence tomography (OCT) mode, or a focal length implementing an NA and a DOF suitable for an optical coherence microscopy (OCM) mode.

According to another aspect of the exemplary embodiment, a medical apparatus includes: a light source; any one of the above-described varifocal lenses configured to focus light from the light source onto an object; and a controller configured to control the varifocal lens to adjust a focal length of the varifocal lens.

According to another aspect of the exemplary embodiment, the medical apparatus may further include an optical fiber scanner configured to horizontally scan the light from the light source unit to the object.

According to another aspect of the exemplary embodiment, the medical apparatus may further include a signal processor configured to process a signal received from the object.

According to another aspect of the exemplary embodiment, the medical apparatus may further include an optical interferometer configured to split the light from the light source to generate a reference beam and a measurement beam that is coherent light, wherein the signal processor may generate an optical coherence tomography (OCT) image by using the reference beam and the measurement beam reflected or scattered from the object.

The light source may include a pulse laser configured to induce an ultrasonic wave from the object, wherein the signal processor may generate an ultrasonic image by using the ultrasonic wave generated from the object.

According to another exemplary embodiment of the application, a multi-mode variable focal length optical scanning apparatus comprises a first fluidic lens which has a first lens surface with a variable curvature and a first pressure surface, and a second fluidic lens which has a second lens surface with a variable curvature, and a second pressure surface, wherein a focal length of the apparatus is varied to provide a first numerical aperture (NA) and a first depth of focus (DOF) for an optical coherence tomography mode, and the focal length of the apparatus is varied to provide a second NA and a second DOF for an optical coherence microscopy mode.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION OF EXEMPLARY EMBODIMENTS

Figure 1:
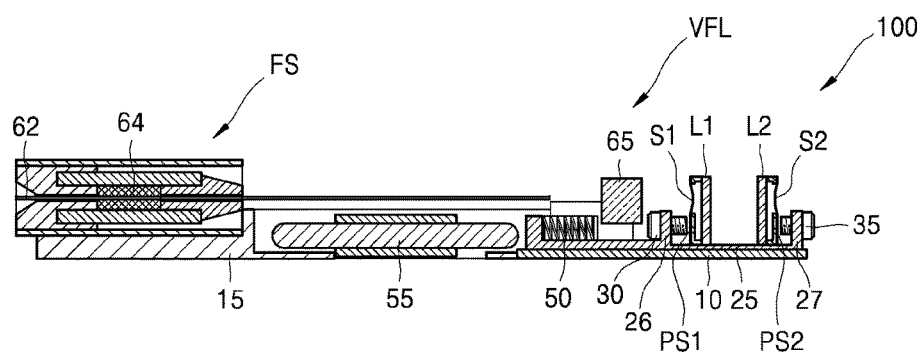
FIG. 1 is a cross-sectional view illustrating a schematic structure of an optical scanning probe according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, expressions such as "at least one of," when preceding a list of elements, modify the entire list of elements and do not modify the individual elements of the list.

Hereinafter, exemplary embodiments will be described in detail with reference to the accompanying drawings. In the drawings, like reference numerals denote like elements, and the sizes of components may be exaggerated for clarity.

Figure 2:
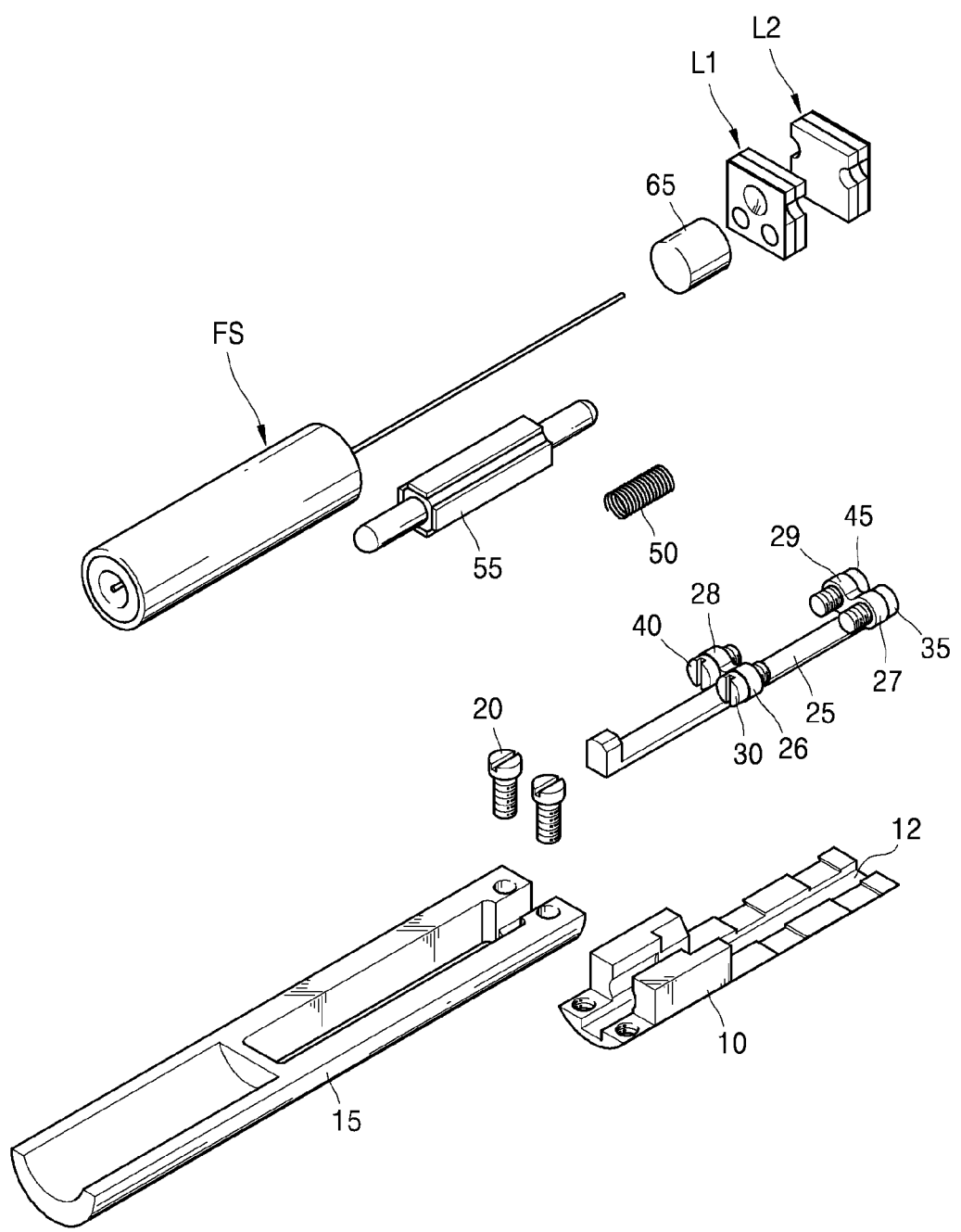
FIG. 2 is an exploded perspective view illustrating components of the optical scanning probe according to an exemplary embodiment.
Figure 3:
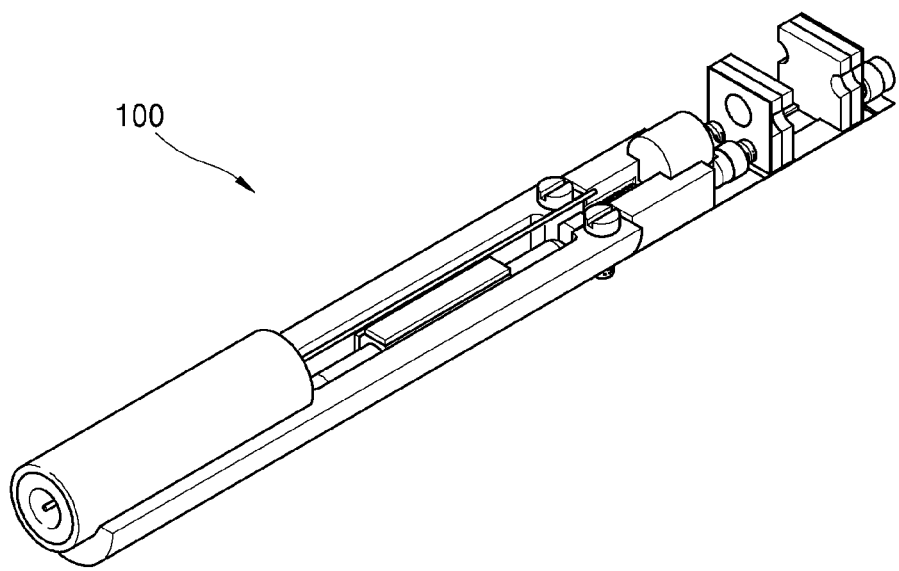
FIG. 3 is a perspective view illustrating an external shape of the optical scanning probe according to an exemplary embodiment.
Figure 4:
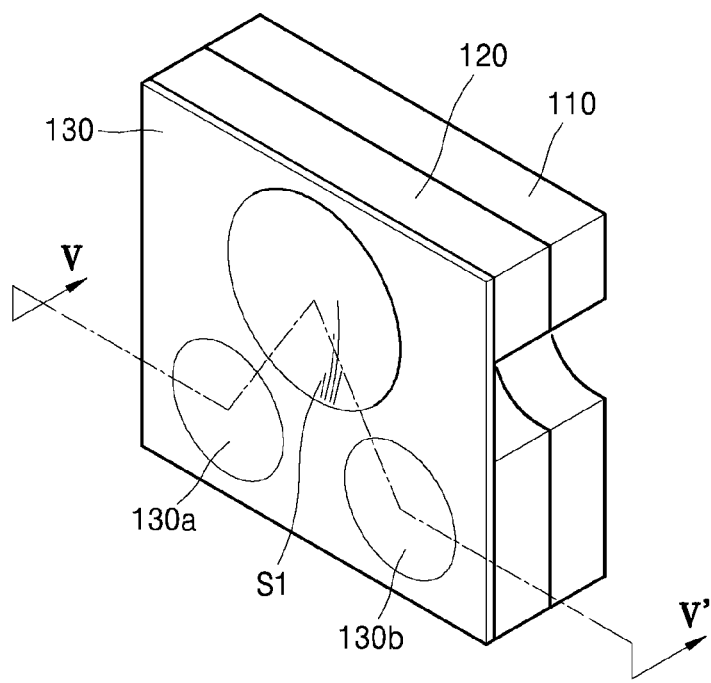
FIG. 4 is a perspective view illustrating a schematic structure of a membrane lens included in the optical scanning probe of FIG. 1.
Figure 5A:
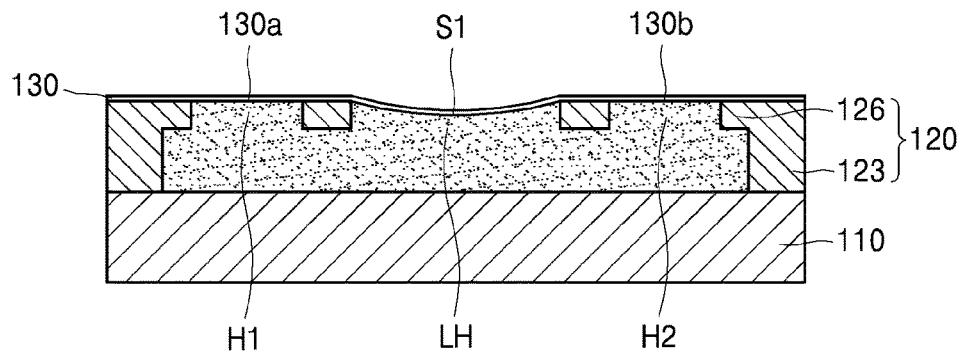
FIGS. 5A to 5C are cross-sectional views taken along line V-V' of FIG. 4, which illustrate an initial state of a lens surface and a state in which a curvature of the lens surface is varied by a driving operation of a motor.
Figure 5B:
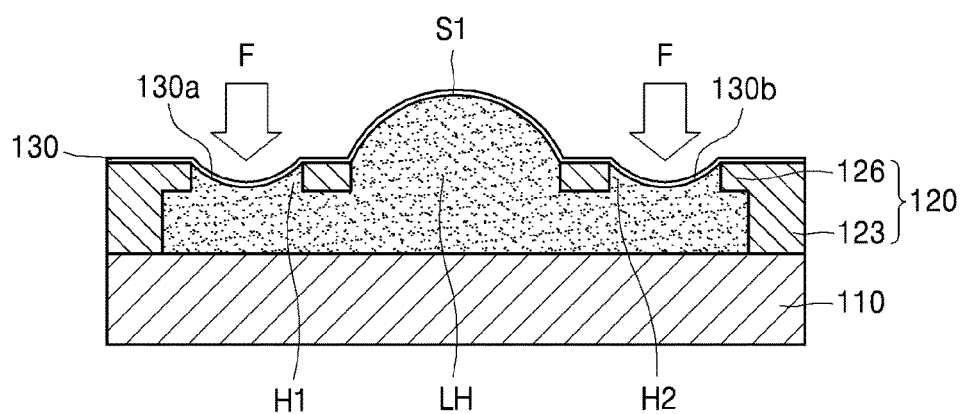
Figure 5C:
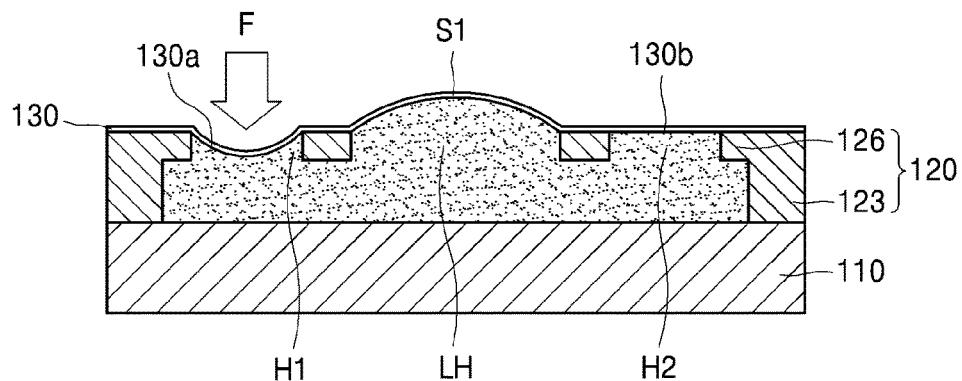

FIG. 1 is a cross-sectional view illustrating a schematic structure of an optical scanning probe 100 according to an exemplary embodiment. FIG. 2 is an exploded perspective view illustrating components of the optical scanning probe 100 according to an exemplary embodiment. FIG. 3 is a perspective view illustrating an external shape of the optical scanning probe 100 according to an exemplary embodiment. FIG. 4 is a perspective view illustrating a schematic structure of a membrane lens included in the optical scanning probe 100 of FIG. 1. FIGS. 5A to 5C are cross-sectional views taken along line V-V' of FIG. 4, which illustrate an initial state of a lens surface and a state in which a curvature of the lens surface is varied by a driving operation of a motor.

The optical scanning probe 100 is a varifocal optical scanning probe and includes an optical fiber scanner (FS) and a varifocal lens (VFL).

The optical fiber scanner FS is configured to scan and irradiate light from a light source to a predetermined position. The optical fiber scanner (FS) may include an optical fiber 62 configured to transmit light, and an actuator 64 configured to modify the optical fiber 62. For example, the actuator 64 may be a piezoelectric actuator using a piezoelectric material that is modified according to an electrical signal, but it is not limited thereto.

The varifocal lens (VFL) is configured to focus light from the optical fiber scanner (FS) onto an object, wherein a focal length thereof is variable. To this end, the varifocal lens (VFL) includes a first membrane lens L1 having a first lens surface S1 with a variable curvature and a first pressure surface PS1 configured to induce a curvature variation of the first lens surface S1, a second membrane lens L2 having a second lens surface S2 with a variable curvature and a second pressure surface PS2 configured to induce a curvature variation of the second lens surface S2, a first pressure member 30 configured to apply a pressure to the first pressure surface PS1, a second pressure member 35 configured to apply a pressure to the second pressure surface PS2, and a motor 55 configured to transmit a driving force to the first pressure member 30 and the second pressure member 35. The motor 55 may be a motor generating a linear driving force.

The first and second membrane lenses L1 and L2 are lenses that include a fluid flow space and an elastic membrane, and are configured to vary a curvature of a lens surface based on a shape modification of the elastic membrane caused by a fluid flow. For example, referring to FIGS. 4 and 5A, the first membrane lens L1 and the second membrane lens L2 include a transparent substrate 110, a spacer 120, and a membrane 130. The spacer 120 is disposed on the transparent substrate 110. The spacer 120 includes a member 123 configured to surround a circumference portion of the transparent substrate 110 and form an internal space, and a member 126 configured to cover a top portion of the internal space and having a lens hole LH formed at a center thereof and two through-holes H1 and H2 formed adjacent to the lens hole LH.

A fluid is disposed in the internal space, and the internal space is sealed by the membrane 130. The membrane 130 includes a first lens surface S1 configured to cover the lens hole LH of the spacer 120, and pressure surfaces 130a and 130b configured to respectively cover the two through-holes H1 and H2 of the spacer 120. The pressure surfaces PS1 (130a) and PS2 (130b) are configured to induce a curvature variation of the first lens surface S1. The first and second pressure surfaces PS1 and PS2 may be the pressure surfaces 130a and 130b respectively. When a pressure is applied to the pressure surfaces 130a and 130b, the pressure surfaces 130a and 130b are modified. Accordingly, the fluid moves to the first lens surface S1 and thus the curvature of the first lens surface S1 varies.

FIG. 5A illustrates a state in which a pressure generated by the linear driving force of the motor 55 is not applied to the pressure surfaces 130a and 130b. However, the illustrated curvature of the first lens surface S1 is merely exemplary, and the exemplary embodiments are not limited thereto.

FIG. 5B illustrates a state in which a pressure generated by the linear driving force of the motor 55 is applied to the pressure surfaces 130a and 130b. When the pressure surfaces 130a and 130b are modified based on the pressure applied to them by the linear driving force of the motor 55, the fluid in the internal space corresponding to the locations of the pressure surfaces 130a and 130b, moves to the first lens surface S1 and thus the first lens surface S1 is formed into a convex shape.

The linear driving force of the motor 55 may be applied to only any one of the two pressure surfaces 130a and 130b. FIG. 5C illustrates a state in which a pressure generated by the linear driving force of the motor 55 is applied only to the pressure surface 130a. The pressure surface 130b may be configured to provide the curvature of the first lens surface S1 in an initial state in which the linear driving force of the motor 55 is not applied to the pressure surface 130a. That is, although the pressure surface 130b is illustrated as being flat, the pressure surface 130b may also be slightly convexed or concaved.

Although FIGS. 5A to 5C illustrate the first lens surface S1 of the first membrane lens L1 as an example, the second lens surface S2 of the second membrane lens L2 may also be modified in the same manner.

Although FIGS. 4 and 5A to 5C illustrate the membrane lens having two pressure surfaces, this is merely exemplary and the membrane lens may also have one pressure surface or three or more pressure surfaces.

A detailed configuration for modifying the first and second lens surfaces S1 and S2 of the first and second membrane lenses L1 and L2 by driving the motor 55 will be described below with reference to FIGS. 1 and 2.

The first pressure member 30 and the second pressure member 35 are mounted on a slider 25 such that the first pressure member 30 and the second pressure member 35 are spaced apart from each other by a predetermined distance in a linear movement direction of the motor 55.

A first fixing member 26 and a second fixing member 27, which are configured to respectively secure the first pressure member 30 and the second pressure member 35 onto the slider 25, may be attached to the slider 25. As illustrated, the first pressure member 30 and the second pressure member 35 may be screw-shaped and may be inserted and fastened into the first fixing member 26 and the second fixing member 27. However, the exemplary embodiments are not limited thereto.

The disposition of the first pressure member 30 and the second pressure member 35 is determined to correspond to the disposition of the first membrane lens L1 and the second membrane lens L2. As illustrated, the first membrane lens L1 and the second membrane lens L2 may be disposed such that the first lens surface S1 and the second lens surface S2 face in opposite directions. Accordingly, the first pressure member 30 and the second pressure member 35 may be disposed to respectively apply a pressure to the first and second pressure surfaces PS1 and PS2 of the respective first and second membrane lenses L1 and L2. As illustrated, both the first and second membrane lens L1 and L2 may be disposed between the first pressure member 30 and the second pressure member 35.

A third fixing member 28 may be connected to the first fixing member 26, and a fourth fixing member 29 may be connected to the second fixing member 27. A third pressure member 40 and a fourth pressure member 45 may be respectively mounted on the slider 25 by the third fixing member 28 and the fourth fixing member 29. As illustrated, the third pressure member 40 and the fourth pressure member 45 may be screw-shaped and may be inserted and fastened into the third fixing member 28 and the fourth fixing member 29; however, the exemplary embodiments are not limited thereto.

This configuration simultaneously applies pressure to the two pressure surfaces 130a and 130b provided respectively in the first and second membrane lenses L1 and L2, and the first and second membrane lenses L1 and L2 may be modified into the shapes of FIGS. 5A and 5B.

On the other hand, the third fixing member 28 and the fourth fixing member 29 may not be mounted on the slider 25. In FIG. 2, the first fixing member 26 and the third fixing member 28 are connected to each other and the second fixing member 27 and the fourth fixing member 29 are connected to each other. However, this is simply exemplary, and they may be separated from each other unlike the illustrated shape. In this case, when the motor 55 is driven, only the first pressure member 30 and the second pressure member 35 mounted on the slider 25 receive the linear driving force of the motor 55. Therefore, the linear driving force of the motor 55 may be transmitted to only one of the two pressure surfaces 130a and 130b provided respectively in the first and second membrane lenses L1 and L2, and the first and second membrane lenses L1 and L2 may be modified into the shapes of FIGS. 5A and 5C. In this case, the third pressure member 40 and the fourth pressure member 45 may apply a pressure to the other one of the two pressure surfaces 130a and 130b provided respectively in the first and second membrane lenses L1 and L2, to determine an initial curvature of the first lens surface S1 and the second lens surface S2. The level of the pressure applied may be adjusted simply by the rotation of the screw.

Since the second fixing member 27 and the fourth fixing member 29 should be disposed to face any one of the two pressure surfaces 130a and 130b provided respectively in the first and second membrane lenses L1 and L2, the second fixing member 27 is disposed in parallel to the first fixing member 26 and the fourth fixing member 29 is disposed in parallel to the third fixing member 28, as illustrated. However, the fourth fixing member 29 is fixed to a position to which the linear driving force is not transmitted, and may be fixed, for example, onto a lens base 10.

An elastic or spring member 50 may be disposed at one end of the slider 25. When the linear driving force is transmitted from the motor 55 and the slider 25 moves forward, the elastic member 50 is contracted; and when the linear driving force is not transmitted from the motor 55, the elastic member 50 is restored to an original state to move the slider 25 backward. As illustrated, the elastic member 50 may be a spring, and one end of the spring may be fixed to one end of the slider 25. However, the elastic member 50 is not limited to a spring.

For the above operation of the elastic member 50, a support member may be provided to support the contraction of the elastic member 50. The support member may be a graded index (GRIN) lens 65 disposed between the elastic member 50 and the first pressure member 30. The GRIN lens 65 has an internal refractive index that changes gradually. Therefore, since an incident light undergoes a path change according to a refractive index change, the GRIN lens 65 may implement a lens function while having a flat shape in which an entrance surface and an exit surface have no curvature. The GRIN lens 65 is provided to correct the aberration of the first and second membrane lenses L1 and L2. However, the number and the shape of GRIN lenses 65 are not limited to the illustrated configuration.

The GRIN lens 65, the first membrane lens L1, and the second membrane lens L2 may be assembled on the lens base 10. The lens base 10 is configured to fix the GRIN lens 65, the first membrane lens L1, and the second membrane lens L2, and has a groove portion 12 that is recessed such that the slider 25 may move linearly by being inserted thereinto.

An assembly process of the optical scanning probe 100 will be described below.

The slider 25, to which the elastic member 50 and the first to fourth pressure members 30, 35, 40 and 45 are attached, is inserted into the groove portion 12 of the lens base 10, and the GRIN lens 65, the first membrane lens L1, and the second membrane lens L2 are fixed to predetermined positions. Herein, the first membrane lens L1 and the second membrane lens L2 may be disposed on the lens base 10 such that the first lens surface S1 and the second lens surface S2 face in opposite directions, and the first to fourth pressure members 30, 35, 40 and 45 may be correspondingly disposed on the slider 25.

A motor base 15, on which the optical fiber scanner FS and the motor 55 may be mounted, is prepared and is connected to the lens base 10 by a screw member 20, and the optical fiber scanner FS and the motor 55 are attached to the base motor 15, thereby completing an assembly as illustrated in FIG. 3.

Figure 6A:
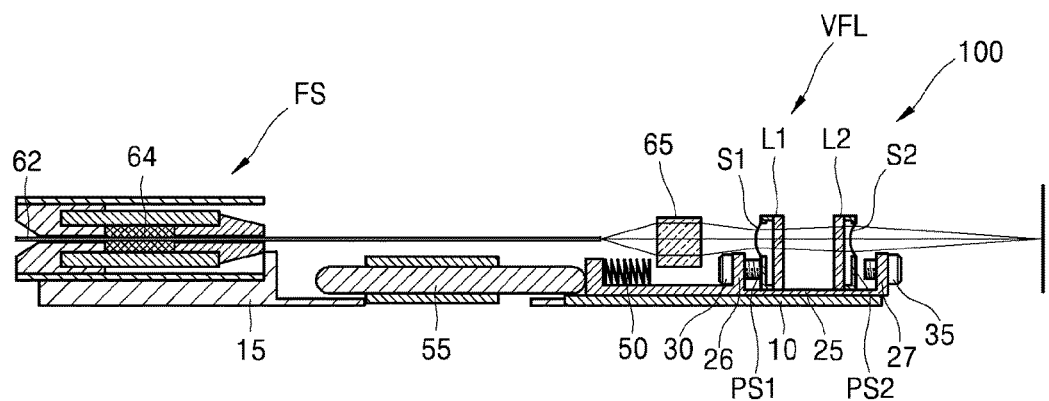
FIGS. 6A and 6B are cross-sectional views illustrating that the optical scanning probe according to an exemplary embodiment operates in an optical coherence microscopy (OCM) mode and in an optical coherence tomography (OCT) mode.
Figure 6B:
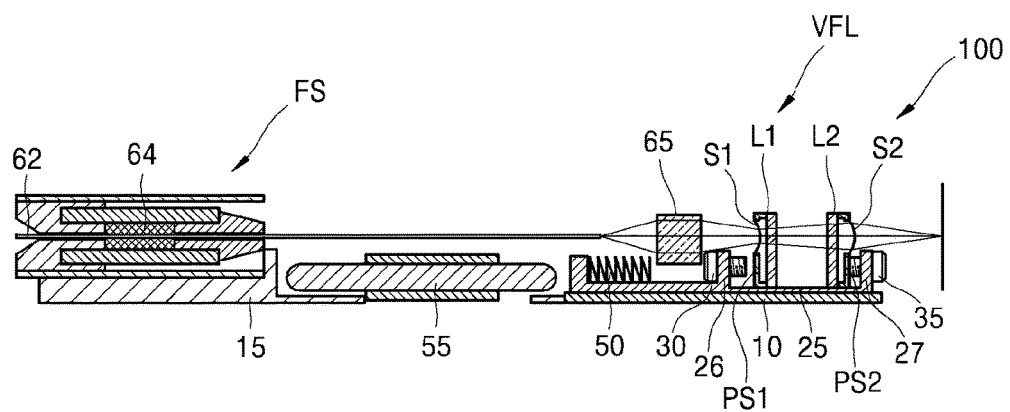
Figure 7:
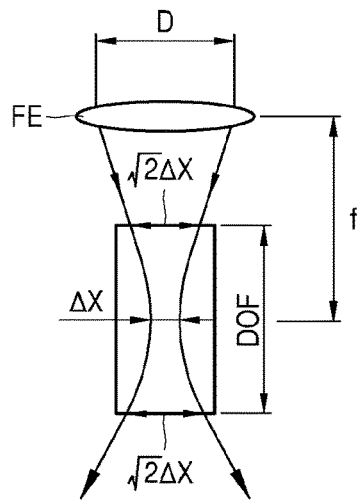
FIG. 7 is a conceptual diagram illustrating a relation between horizontal resolution and depth of focus (DOF), depending on a numerical aperture (NA) that is generally determined by a focusing optical member.

FIGS. 6A and 6B are cross-sectional views illustrating that the optical scanning probe 100 according to an exemplary embodiment operates in an optical coherence microscopy (OCM) mode and in an optical coherence tomography (OCT) mode. FIG. 7 is a conceptual diagram illustrating a relation between horizontal resolution and depth of focus (DOF), depending on a numerical aperture (NA) that is generally determined by a focusing optical member.

FIG. 6A illustrates a state in which the motor 55 is driven to transmit a forward driving force to the slider 25. By the above disposition structure of the first pressure member 30 and the second pressure member 35, the first pressure member 30 applies a pressure to the first pressure surface PS1 of the first membrane lens L1 and the second pressure member 35 recedes from the second pressure surface PS2 of the second membrane lens L2. Accordingly, the first lens surface S1 is deformed into a convex shape, and the second lens surface S2 is deformed into a concave shape. The elastic member 50 is contracted.

FIG. 6B illustrates a state in which the motor 55 does not transmit a forward driving force to the slider 25. The elastic member 50, which was contracted in FIG. 6A is restored to an original shape, and the slider 25 is driven backward by the restoration force. Accordingly, the second pressure member 35 applies a pressure to the second pressure surface PS2 and the first pressure member 30 recedes from the first pressure surface. Thus, the second surface S2 is deformed into a convex shape, and the first lens surface S1 is deformed into a concave shape.

Due to this modification of the first and second membrane lenses L1 and L2, the focal length of the varifocal lens VFL varies, and the exemplary embodiment of FIG. 6A implements a longer focal length than the exemplary embodiment of FIG. 6B.

The focal length may be determined suitably according to the purposes of the optical scanning probe 100. In detail, the focal length may be determined to provide an NA and a DOF suitable for the purpose of the optical scanning probe 100. For example, in FIG. 6A, the focal length may be determined to provide an NA and a DOF suitable for the OCT mode, and in FIG. 6B, the focal length may be determined to provide an NA and a DOF suitable for the OCM mode. For this operation, the optical scanning probe 100 may include a controller configured to control the motor 55 such that the focal length of the varifocal lens VFL corresponds to the focal length implementing the NA and the DOF suitable for the OCT mode, or the focal length implementing the NA and the DOF suitable for the OCM mode.

The NA and the DOF will be described below in brief with reference to FIG. 7.

When a beam is focused, the beam is focused, not on a point, but on a finite range of Δx. Δx is determined by an aperture "D" and a focal length "f" according to Equation 1 below.

$$\Delta x = \frac{4}{\pi}\lambda \frac{f}{D} \quad \text{[Equation 1]}$$

Δx is related to horizontal resolution. The horizontal resolution increases as Δx decreases. As expressed in Equation 1, Δx is proportional to f/D. Since the NA is proportional to D/f, an optical system having a small Δx, that is, high horizontal resolution has a large NA and a short focal length.

The DOF is defined as a range in which a beam diameter is $\sqrt{2}$ Δx and determined according to Equation 2 below.

$$DOF = \frac{\pi}{2\lambda}(\Delta x)^2 \quad \text{[Equation 2]}$$

The DOF represents a range in which a beam spot size is relatively uniform in a depth direction. An optical system having a large DOF is required to capture depth-dependent image information, for example, a tomographic image of a human body tissue. The optical system having a large DOF has a small NA and a long focal length.

In this manner, the horizontal resolution and the DOF have a trade-off relation, and an optical system having an NA and a focal length suitable for the purpose of a test is required. For example, a microscope needs an optical system having a high NA for high horizontal resolution, and OCT needs an optical system in which a spot size is relatively uniform in a depth direction, that is, an optical system having a large DOF and a low NA, in order to acquire depth information.

The optical scanning probe according to an exemplary embodiment may implement various focal lengths by varying the curvatures of the two membrane lenses, thus making it possible to implement various DOFs and NAs.

FIGS. 6A and 6B illustrate that the optical scanning probe according to an exemplary embodiment may operate in two modes, that is, the OCT mode and the OCM mode. However, this is merely exemplary, and the optical scanning probe may be configured to operate as a multi-mode probe by diversifying the initial curvatures of the first and second membrane lenses L1 and L2 and the operation steps of the motor 55.

Figure 8:
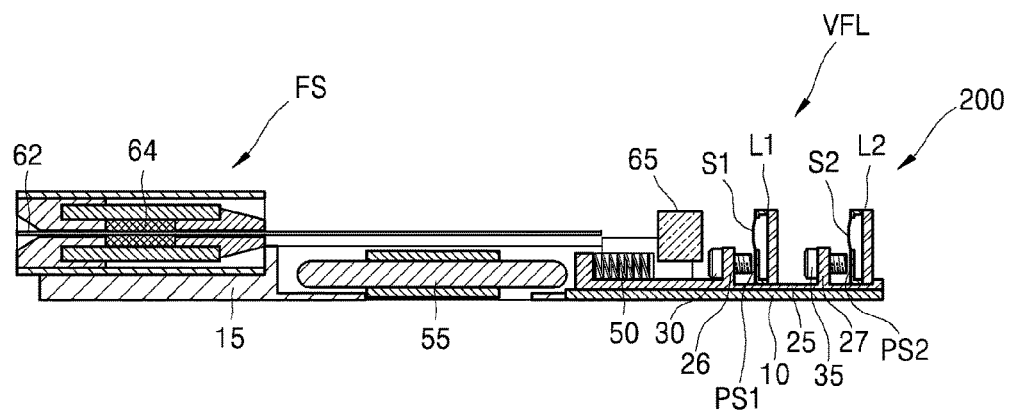
FIG. 8 is a cross-sectional view illustrating a schematic structure of an optical scanning probe according to another exemplary embodiment.

FIG. 8 is a cross-sectional view illustrating a schematic structure of an optical scanning probe 200 according to another exemplary embodiment.

The optical scanning probe 200 is different from the optical scanning probe 100 of FIG. 1 in terms of the disposition of the first and second membrane lenses L1 and L2 and the disposition of the first and second pressure members 30 and 35.

Unlike FIG. 1, the first membrane lens L1 and the second membrane lens L2 are disposed such that the first lens surface S1 and the second lens surface S2 face in the same direction.

In this case, the first pressure member 30 and the second pressure member 35 are disposed on the slider 25 such that the first pressure member 30 applies a pressure to the first pressure surface PS1 and the second pressure member 35 applies a pressure to the second pressure surface PS2 when the motor 55 is driven forward.

Figure 9:
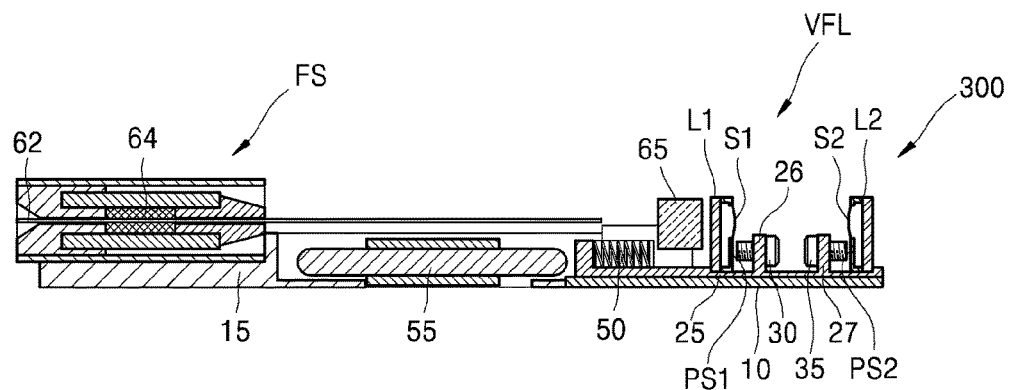
FIG. 9 is a cross-sectional view illustrating a schematic structure of an optical scanning probe according to another exemplary embodiment.

FIG. 9 is a cross-sectional view illustrating a schematic structure of an optical scanning probe 300 according to another exemplary embodiment.

The optical scanning probe 300 is different from the optical scanning probe 100 of FIG. 1 and FIG. 9 in terms of the disposition of the first and second membrane lenses L1 and L2 and the disposition of the first and second pressure members 30 and 35.

Unlike FIG. 1, the first membrane lens L1 and the second membrane lens L2 are disposed such that the first lens surface S1 and the second lens surface S2 face each other.

In this case, the first pressure member 30 and the second pressure member 35 are disposed on the slider 25 such that the second pressure member 35 applies a pressure to the second pressure surface PS2 and the first pressure member 30 recedes from the first pressure surface PS1 when the motor 55 is driven forward.

Figure 10:
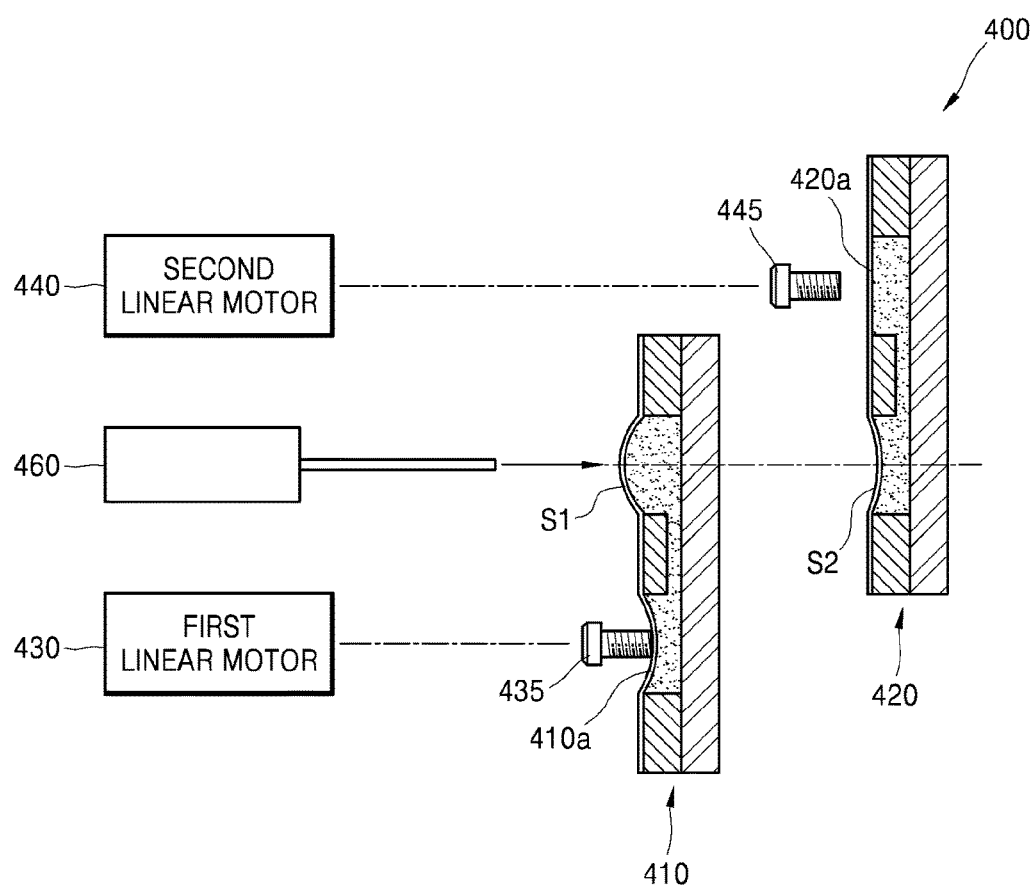
FIG. 10 is a block diagram illustrating a schematic configuration of an optical scanning probe according to another exemplary embodiment.

FIG. 10 is a block diagram illustrating a schematic configuration of an optical scanning probe 400 according to another exemplary embodiment.

The optical scanning probe 400 is different from the optical scanning probes 100, 200 and 300 in that the first and second membrane lenses L1 and L2 are adjusted separately.

The optical scanning probe 400 includes a first membrane lens 410, a first pressure member 435 configured to apply a pressure to a first pressure surface 410a of the first membrane lens 410, a first motor 430 configured to transmit a linear driving force to the first pressure member 435, a second membrane lens 420, a second pressure member 445 configured to apply a pressure to a second pressure surface 420a of the second membrane lens 420, and a second motor 440 configured to transmit a linear driving force to the second pressure member 445.

The first membrane lens 410 and the second membrane lens 420 are spaced apart from each other in a direction of the linear driving force and a direction perpendicular to the direction of the linear driving force. As illustrated, a first lens surface S1 and a second lens surface S2 are disposed in a direction (Z direction) of an optical axis of light irradiated by an optical fiber scanner 460, the first pressure surface 410a is disposed to be spaced apart from the optical axis in a −X direction, and the second pressure surface 420a is disposed to be spaced apart from the optical axis in a +X direction.

FIG. 10 illustrates that the first pressure surface 410a is pressurized on the basis of the pressure applied by the first pressure member 435, and the second pressure surface 420a is not pressurized, but this is merely exemplary. Since the first motor 430 and the second motor 440 are driven separately, both the first pressure surface 410a and the second pressure surface 420a may be pressurized or may not be pressurized or only the first pressure member 435 or second pressure surface 420a may be pressurized.

In the case of the optical scanning probes 100, 200 and 300 according to the above exemplary embodiments, since they are driven by one motor 55, the curvature of the first lens surface S1 and the curvature of the second lens surface S2 are not independent of each other but have a predetermined relation therebetween. Therefore, a focal length range to be implemented may be restricted.

In the present exemplary embodiment, since the curvature of the first lens surface S1 and the curvature of the second lens surface S2 may be adjusted separately, more various ranges of focal lengths may be implemented.

The first and second membrane lenses 410 and 420 may be configured to have one pressure surface, or may be configured to have two pressure surfaces as illustrated in FIG. 4. For example, although not illustrated, the first and second membrane lenses 410 and 420 may further include a third pressure surface and a fourth pressure surface that are spaced apart from the first pressure surface 410a and the second pressure surface 420a in a −Y direction, respectively. In this case, pressure members may be further provided to apply pressure to the third pressure surface and the fourth pressure surface. The pressure members may be driven together with the first and second pressure members 435 and 445 by the first and second motors 430 and 440, or may be used to adjust the initial curvatures of the first and second lens surfaces S1 and S2.

Although the present exemplary embodiment is illustrated in the form of a block diagram, the configurations such as the lens base 10, the slider 25, and the motor base 15 illustrated in the exploded perspective view of FIG. 2 may be suitably modified for use in the present exemplary embodiment.

The above-described varifocal lens VFL may focus light on an object, for example, on a predetermined position in a living body such as a human body, and may be used in various types of medical apparatuses together with a light source and a controller configured to control the varifocal lens VFL to adjust the focal length of the varifocal lens VFL. The medical apparatuses may further include a signal processor configured to process a signal received from the object. Various types of medical imaging apparatuses may be implemented according to the types of light irradiated to the object and the methods of processing a signal received from the object.

Figure 11:
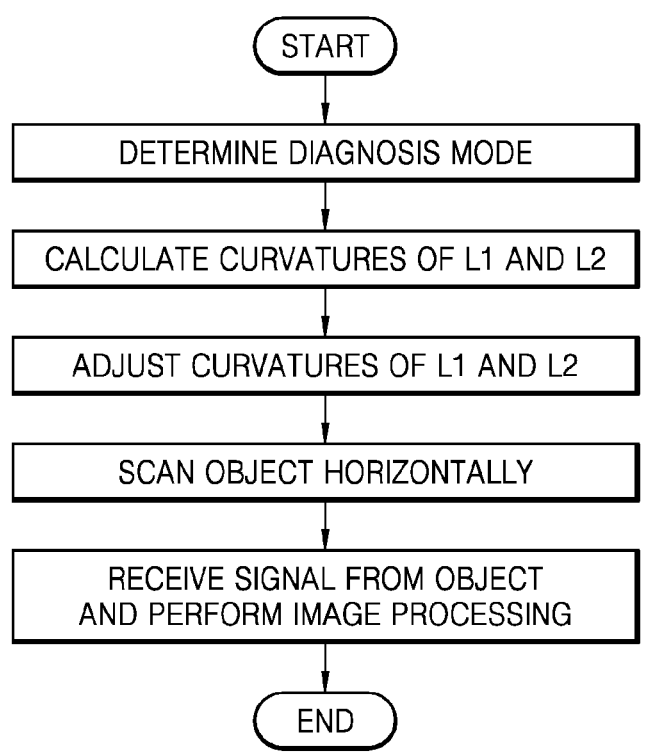
FIG. 11 is a flowchart illustrating a schematic operation process of a medical imaging apparatus including an optical scanning probe according to an exemplary embodiment.

FIG. 11 is a flowchart illustrating a schematic operation process of a medical imaging apparatus including the optical scanning probe according to an exemplary embodiment.

First, the medical imaging apparatus determines a diagnosis mode of an object. When the optical scanning probe is set to operate in any one of the OCT mode and the OCM mode, this operation may be an operation of selecting one of the two modes or an operation of inputting a desired focal length.

The medical imaging apparatus calculates the curvatures of the lens surfaces of the membrane lenses L1 and L2 based on input information.

Based on the calculation result, the medical imaging apparatus drives the motor to adjust the curvatures of the membrane lenses L1 and L2 based on the selected mode.

Thereafter, the medical imaging apparatus horizontally scans the object within a set focal length by using the optical fiber scanner, irradiates light, receives light from the object, and performs necessary image processing.

Figure 12:
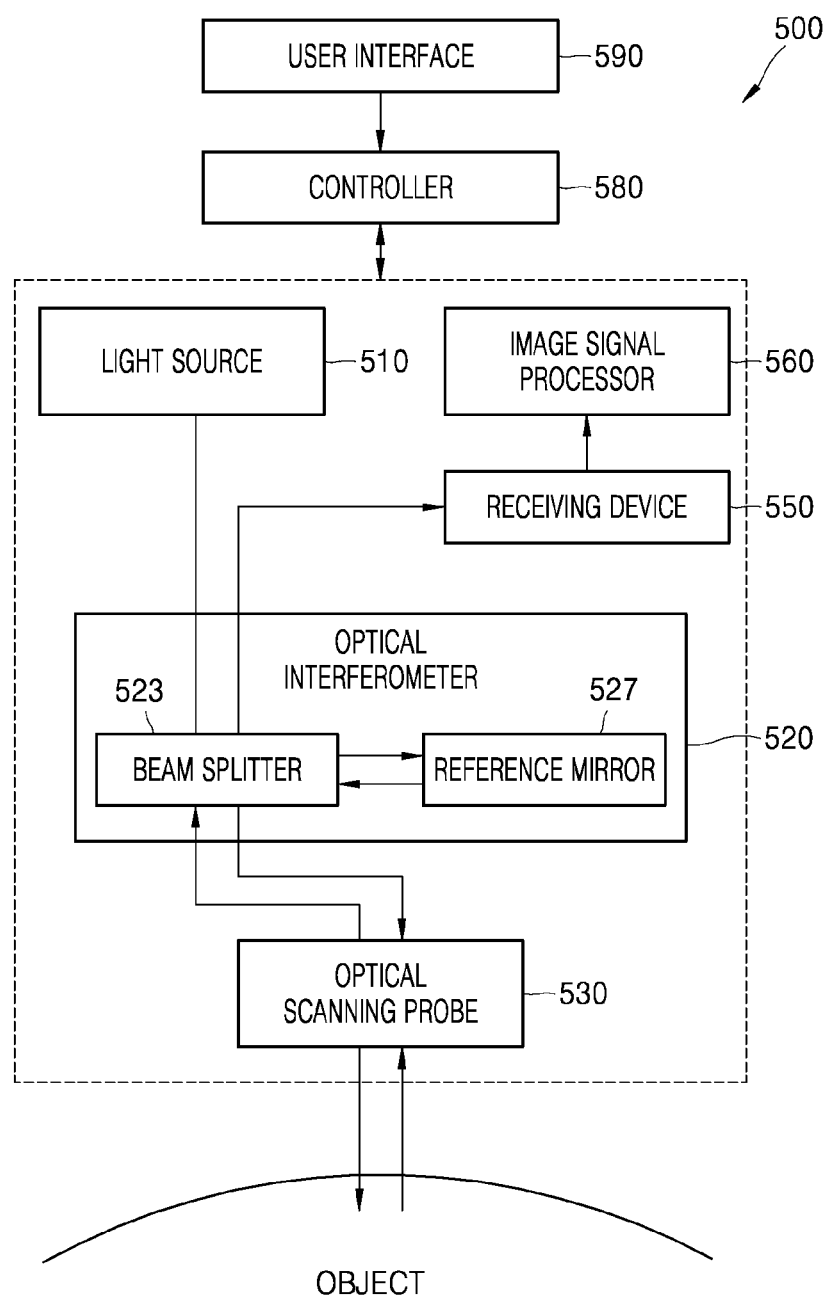
FIG. 12 is a block diagram illustrating a schematic configuration of a medical imaging apparatus according to an exemplary embodiment.

FIG. 12 is a block diagram illustrating a schematic configuration of a medical imaging apparatus 500 according to an exemplary embodiment.

The medical imaging apparatus 500 includes a light source 510, an optical scanning probe 530 configured to scan and irradiate light from the light source 510 onto an object, a controller 580 configured to control a motor of the optical scanning probe 530 to adjust a focal length of a varifocal lens, a receiving device 550 configured to receive a signal generated from the object, and an image signal processor 560 configured to generate an image signal by processing the signal received by the receiving device 550.

The medical imaging apparatus 500 may further include an optical interferometer 520 configured to split the light from the light source 510 into a reference beam and a measurement beam and generate coherent light after the reference beam and the measurement beam are reflected and returned from a mirror and a sample. The optical interferometer 520 includes a reference mirror 527 and a beam splitter 523. The light irradiated by the light source 510 is split into beams by the beam splitter 523 and one of the beams is reflected by the reference mirror 527. The other beam generated by the beam splitter 523 is reflected and returned from the sample. That is, the light reflected from the reference mirror 527 and the sample passes through the beam splitter 523 and then forms coherent light. The coherent light is used as the measurement beam and is converted into an image through the receiving device 550 and the image signal processor 560.

The optical scanning probe 530 is configured to scan a predetermined region of the object and irradiate light. For example, any one or a combination of the above-described optical scanning probes 100, 200, 300 and 400 may be used.

The measurement beam reflected or scattered from the object is split by the beam splitter 523 and is transmitted to the receiving device 550. The image signal processor 560 generates an OCT image based on the measurement beam and the reference beam that are reflected or scattered and received from the object.

The medical imaging apparatus 500 may further include a user interface 590. The user interface 590 may include an input device and a display that may be used to transmit necessary inputs to the controller 580.

The controller 580 controls the respective components of the medical imaging apparatus 500 according to commands input through the user interface 590. For example, the optical scanning probe 530 may control scanner driving and varifocal driving. For example, the controller 580 may be implemented by a microprocessor.

Figure 13:
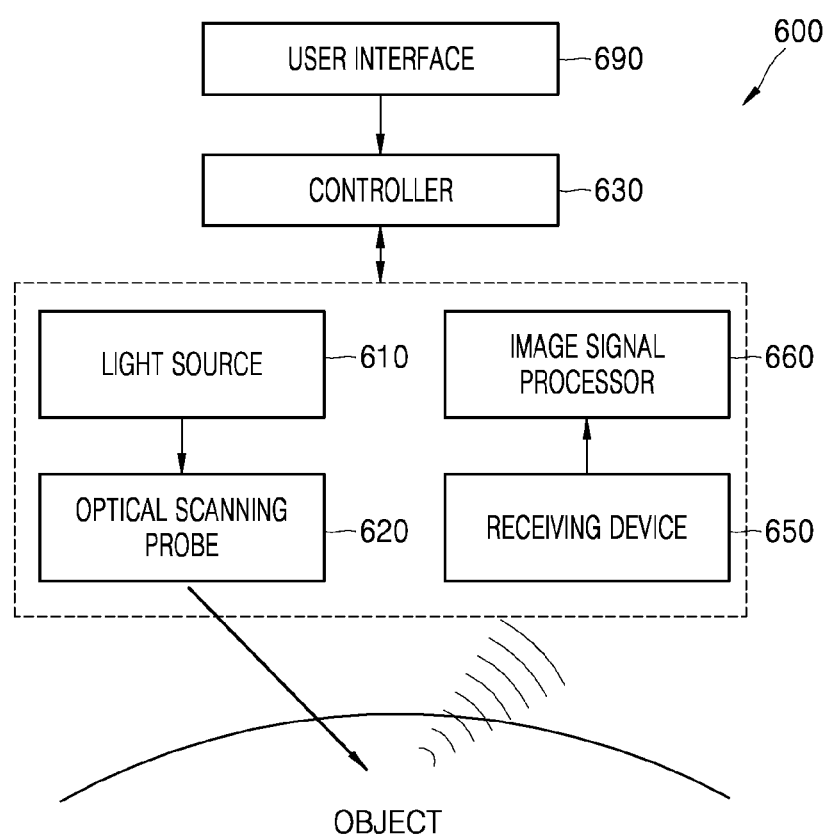
FIG. 13 is a block diagram illustrating a schematic configuration of a medical imaging apparatus according to another exemplary embodiment.

FIG. 13 is a block diagram illustrating a schematic configuration of a medical imaging apparatus 600 according to another exemplary embodiment.

The medical imaging apparatus 600 includes a light source 610, an optical scanning probe 620 configured to scan and irradiate light from the light source 610 onto an object, a controller 630 configured to control a motor of the optical scanning probe 620 to adjust a focal length of a varifocal lens, a receiving device 650 configured to receive a signal generated from the object, and an image signal processor 660 configured to generate an image signal by processing the signal received by the receiving device 650.

For example, the medical imaging apparatus 600 uses photoacoustic tomography (PAT). PAT is technology for implementing an image by sensing a pressure wave that is generated by laser pulse irradiation at a cellular tissue. When a laser is irradiated onto a material such as a liquid or a solid, the material absorbs light energy to generate instantaneous thermal energy. This energy generates an acoustic wave by a thermoelastic phenomenon. Since a thermoelastic coefficient and an absorption rate depending on the wavelength of light vary according to a material forming a test object, different amplitudes of ultrasonic waves are generated with respect to the same light energy. By detecting such ultrasonic waves, images about a change in the characteristics of a minute tissue and the distribution of blood vessels in a human body may be implemented in a non-invasive manner.

The light source 610 may be a pulse laser that induces an ultrasonic wave from the test object, and a pulse width may be several picoseconds to several nanoseconds.

The optical scanning probe 620 is configured to scan a predetermined region of the object and irradiate light. For example, any one or a combination of the above-described optical scanning probes 100, 200, 300 and 400 may be used.

When light is irradiated onto the object through the optical scanning probe 620, an ultrasonic wave is generated from the object. Different frequency bands or different amplitudes of ultrasonic waves are generated according to the pulse width of the laser, the pulse fluence of the laser, the laser absorption coefficient of the object, the reflection coefficient, the specific heat, and the thermal expansion coefficient thereof. That is, when a pulse laser is irradiated onto the test object, different ultrasonic waves are generated according to the types of the object. By detecting such ultrasonic waves, an image for determining the type of the object may be captured.

The receiving device 650 may be an ultrasonic wave receiving device, and may include, for example, a transducer that converts the ultrasonic wave generated from the test object into an electrical signal. For example, the transducer may be a piezoelectric micromachined ultrasonic transducer (PMUT) that converts an ultrasonic vibration into an electrical signal. The PMUT may include a piezoelectric ceramic material, a single-crystal material, or a compound piezoelectric material that is a compound of a high molecular material and the above materials. In addition, the transducer may be implemented by a capacitive micromachined ultrasonic transducer (CMUT), a magnetic micromachined ultrasonic transducer (MMUT), or an optical ultrasonic detector.

The image signal processor 660 may generate an ultrasonic image by processing the signal received by the receiving device 650.

The medical imaging apparatus 600 may further include a user interface 690. The user interface 690 may include an input device and a display that may be used to transmit necessary inputs to the controller 630.

The controller 630 controls the respective components of the medical imaging apparatus 600 according to commands input through the user interface 690. For example, the optical scanning probe 620 may control scanner driving and varifocal driving. For example, the controller 630 may be implemented by a microprocessor.

It has been described above that the medical imaging apparatuses 500 and 600 use OCT and PAT. However, the medical imaging apparatuses may use OCM, and the optical scanning probes according to the exemplary embodiments may be used in various medical imaging apparatuses such as an endoscope. In this case, the receiving device may include a suitable detection sensor according to the type of the signal generated from the test object, and suitable image signal processing methods may be used.

As described above, according to the one or more of the above exemplary embodiments, the motor and the membrane lenses may be used to provide a varifocal lens that has a small diameter, a noiseless feature, a low-voltage feature, and high reliability and is unsusceptible to gravity.

In the optical scanning probes including the varifocal lens, the distance between the lens and the object is fixed and conversion between the two modes may be performed without moving the probe.

The above-described optical scanning probes may be used in various medical apparatuses such as an OCT imaging apparatus and an ultrasonic imaging apparatus.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of exemplary embodiments as defined by the following claims.

What is claimed is:
1. A varifocal lens comprising:
    a first membrane lens comprising a first lens surface which has a variable curvature and a first pressure surface configured to induce a curvature variation of the first lens surface;
    a second membrane lens comprising a second lens surface which has a variable curvature and a second pressure surface configured to induce a curvature variation of the second lens surface;

a first pressure member configured to apply a pressure to the first pressure surface;

a second pressure member configured to apply a pressure to the second pressure surface;

a motor configured to transmit a driving force to at least one of the first pressure member and the second pressure member, wherein the motor is a linear motor configured to generate a linear driving force;

a slider configured to move in a linear direction according to the linear driving force of the motor, on which the first pressure member and the second pressure member being mounted such that the first pressure member and the second pressure member are spaced apart from each other by a predetermined distance in a linear movement direction of the motor; and an elastic member provided at one end of the slider, the elastic member being contracted when the linear driving force is transmitted from the motor and the slider moves in a first direction, and the elastic member being restored to an original state to move the slider in a second direction, opposite to the first direction, when the linear driving force is not transmitted from the motor.

2. The varifocal lens of claim 1, wherein the first membrane lens and the second membrane lens are configured such that the first lens surface and the second lens surface face in opposite directions.

3. The varifocal lens of claim 2, wherein the first pressure member and the second pressure member are configured on the slider such that the first pressure member pressurizes the first pressure surface and the second pressure member recedes from the second pressure surface when the motor is driven in a first direction.

4. The varifocal lens of claim 1, wherein the first membrane lens and the second membrane lens are configured such that the first lens surface and the second lens surface face in a same direction.

5. The varifocal lens of claim 4, wherein the first pressure member and the second pressure member are configured on the slider such that the first pressure member applies a pressure to the first pressure surface and the second pressure member applies a pressure to the second pressure surface when the motor is driven in a first direction.

6. The varifocal lens of claim 1, wherein the first membrane lens and the second membrane lens are configured such that the first lens surface and the second lens surface face each other.

7. The varifocal lens of claim 6, wherein the first pressure member and the second pressure member are configured on the slider such that the second pressure member applies a pressure to the second pressure surface and the first pressure member recedes from the first pressure surface when the motor is driven in a first direction.

8. The varifocal lens of claim 1, wherein
the first membrane lens further comprises a third pressure surface, and
the second membrane lens further comprises a fourth pressure surface.

9. The varifocal lens of claim 8, further comprising:
a third pressure member configured to apply a pressure to the third pressure surface; and
a fourth pressure member configured to apply a pressure to the fourth pressure surface.

10. The varifocal lens of claim 9, wherein
the first pressure member and the third pressure member are configured in a direction perpendicular to a linear movement direction of the motor, and
the second pressure member and the fourth pressure member are configured in the direction perpendicular to the linear movement direction of the motor.

11. The varifocal lens of claim 10, further comprising a slider configured to move in a linear direction according to a linear driving force of the motor,
wherein the first pressure member and the second pressure member are mounted on the slider such that the first pressure member and the second pressure member are spaced apart from each other by a predetermined distance in the linear movement direction of the motor.

12. The varifocal lens of claim 11, wherein a first fixing member and a second fixing member, which are configured to respectively secure the first pressure member and the second pressure member onto the slider, are attached to the slider.

13. The varifocal lens of claim 12, wherein the third pressure member and the fourth pressure member are not mounted on the slider, and are configured to respectively apply a pressure to the third pressure surface and the fourth pressure surface by a predetermined pressure to form an initial curvature of the first lens surface and an initial curvature of the second lens surface.

14. The varifocal lens of claim 13, wherein
the third pressure member and the fourth pressure member are screw-shaped, and
a third fixing member and a fourth fixing member, which are a screw-fastening type, are provided corresponding to the third pressure member and the fourth pressure member, to adjust a pressure level of the third pressure surface and a pressure level of the fourth pressure surface, respectively.

15. The varifocal lens of claim 1, wherein the motor comprises:
a first motor configured to transmit a linear driving force to the first pressure member; and
a second motor configured to transmit a linear driving force to the second pressure member.

16. The varifocal lens of claim 15, wherein the first membrane lens and the second membrane lens are spaced apart from each other in a direction of the linear driving force and are spaced apart from each other in a direction perpendicular to the direction of the linear driving force.

17. An optical scanning probe comprising:
an optical fiber scanner; and
the varifocal lens of claim 1, configured to focus light from the optical fiber scanner on an object.

18. The optical scanning probe of claim 17, further comprising a controller configured to control the motor such that a focal length of the varifocal lens corresponds to at least one of a focal length which implements a numerical aperture (NA) and a depth of focus (DOF) for an optical coherence tomography (OCT) mode, and a focal length implementing an NA and a DOF for an optical coherence microscopy (OCM) mode.

19. A medical apparatus comprising:
a light source;
the varifocal lens of claim 1 configured to focus light from the light source on an object; and
a controller configured to control the varifocal lens to adjust a focal length of the varifocal lens.

20. The medical apparatus of claim 19, further comprising an optical fiber scanner configured to horizontally scan the light from the light source to the object.

21. The medical apparatus of claim 20, further comprising a signal processor configured to process a signal received from the object.

\* \* \* \* \*